United States Patent [19]

Lawson

[11] 4,393,701

[45] Jul. 19, 1983

[54] YARN TESTER SYSTEM

[75] Inventor: John B. Lawson, Providence, R.I.

[73] Assignee: Lawson-Hemphill, Inc., Central Falls, R.I.

[21] Appl. No.: 344,066

[22] Filed: Jan. 29, 1982

[51] Int. Cl.³ .............................................. G01L 5/04
[52] U.S. Cl. ...................................... 73/160; 73/829; 73/862.44; 242/75.5
[58] Field of Search ............. 73/828, 829, 160, 862.39, 73/862.42, 862.44; 374/49, 50; 242/75.5, 148, 147 R

[56]         References Cited
        U.S. PATENT DOCUMENTS 2,816,758  12/1957  Danly ................................. 242/75.5
3,726,137   4/1973  Denton ................................. 73/160
4,295,252   8/1981  Robinson et al. ................. 73/160 X

OTHER PUBLICATIONS

Continuous Monitoring of Yarn Shrinkage or Stretch, Publication of Lawson-Hemphill, Inc., 1971.

Primary Examiner—Jerry W. Myracle
Attorney, Agent, or Firm—Joseph S. Iandiorio

[57]            ABSTRACT

A yarn tension control for a yarn testing machine includes: a support; a carriage moveable relative to the support; and a tension arm pivotably mounted to the carriage for engaging the yarn. The tension arm is set in a neutral position to apply a predetermined tension to the yarn. Rotation of the arm indicates an incremental change in the yarn tension. Upon such a change in tension the carriage is moved from an initial position to a compensating position to re-establish the predetermined tension. The drive elements then vary the speed of the yarn to produce an offsetting incremental change in the yarn feed rate to restore the tension arm to its neutral position.

32 Claims, 5 Drawing Figures

YARN TESTER SYSTEM

FIELD OF INVENTION

This invention relates to a yarn tester system capable of continuously indicating recovery potential and fiber shrinkage in yarns.

BACKGROUND OF INVENTION

An important characteristic in the evaluation of the quality and performance of textured yarns is crimp recovery potential, which is defined as the amount by which a textured yarn decreases in length in a fully relaxed condition when allowed to retract from the fully extended state. Textured yarn is formed of one or more continuous filaments in a first-set state which are false-twisted, crimped, curled, or otherwise compacted while heated to set a kink into the filaments which will remain when the filaments are cooled. The textured yarn now has a second-set state and has retracted to a shorter overall length, Usually the yarn is wound onto a package, which may in time impose yet another, third set state. This third-set state is eliminated by developing the yarn either while it is still in yarn form or after it has been formed into a fabric. Developing is a technique by which the yarn or fabric made of the yarn is relaxed by heating to a temperature below that used to produce the second-set state while the yarn or fabric is fully relaxed, or at least partially relaxed to some preset standard. During this development process, a second, separate action known as fiber shrinkage may occur due to the heating of the yarn. Thus, while removing the effects of the third-set state or packaging-set state, a real axial shrinkage may be induced. The length of the yarn in the developed relaxed state is thus the original length of the yarn in its fully extended state minus the sum of the crimp recovery plus the fiber shrinkage. The term "relaxed" is used to indicate both a fully relaxed yarn and also a yarn which is lightly tensioned as understood in the art.

A number of attempts have been made to measure recovery potentials in textured yarn. In one approach, the recovery potential of a textured yarn is determined by first developing and then hanging a number of different weights on a skein of yarn to measure skein lengths to calculate crimp recovery and fiber shrinkage. The process is not continuous and requires a substantial amount of time. In another system a fully extended yarn is heated in a zone between two feed roll systems, with the downstream feeder fixed to operate at a predetermined slower feed rate than the upstream feeder so that partial retraction takes place in the test zone. Means are used to measure the tension in the test zone as an indicator of recovery potential, but since the speed of the downstream feeder is fixed at a preset level, it produces only an indication of the yarn's performance under preselected conditions and is not an absolute measure of the yarn's recovery potentials. This approach also does not distinguish the crimp recovery from the fiber shrinkage. The instant inventor proposed a system in which a fully extended yarn was fed into a controlled tension zone and over a heater between upstream and downstream feed rolls. A spring-loaded arm varied the speed of the upstream feeder to maintain the constant tension on the yarn in the test zone, and the rotational speeds of the feed rolls were compared to each other to determine the extent of total retraction that had occurred in the test zone. The device failed to separate crimp recovery and fiber shrinkage and the device was not capable of controlling the tension at low tension levels, e.g. one to two milligrams per denier. In another, two-zone device, development took place in the first zone between two sets of feeders moving at speeds corresponding to the recovery level of the yarn that moved between them. A second zone was established between the second feeder rolls and a third set of feeder rolls. The third set of feeder rolls operated at the same rate as the first set of feeder rolls. A tensiometer engaged the yarn to measure the force required to stretch the yarn in the second zone back to its undeveloped length. An increase in tension in the second zone over and above the initial known input tension would be an indication that there had been some fiber shrinkage. After separate stress-strain studies of the test yarns, approximate shrinkage length might be obtained for specific tension values. The tension determination was extremely sensitive to variations in the input tension to the first feeder. Absolute values of crimp recovery and fiber shrinkage were not obtained, and the system was not sensitive nor reliable enough. For example, the damping required on the tension arm introduced extraneous forces to the yarn tension upon changes in recovery of the yarn. This interfered with uniformity of tension during the yarn development, which uniformity is necessary for meaningful results.

A shortcoming in a number of these devices is the tensioning devices which have been used to attempt to maintain the tension on the yarn which is so necessary for accurate, meaningful results. In the past they have tended to be not sensitive or reliable enough for measuring recovery and shrinkage at low-tension levels. Often damping or other approaches introduced extraneous forces to the yarn tensioning system and interfered with the useful results.

SUMMARY OF THE INVENTION

It is therefore an object of this invention to provide an improved yarn tester system which provides both yarn recovery and fiber shrinkage.

It is a further object of this invention to provide such a system which functions continuously to monitor yarn recovery and shrinkage.

It is a further object of this invention to provide such a system which functions efficiently and uniformly to monitor yarn recovery and shrinkage.

It is a further object of this invention to provide such a system which provides an absolute, not conditional, measure of a yarn's potential recovery and shrinkage.

It is a further object of this invention to provide such a system which is accurate and renders complete recovery potential and shrinkage even at very low tension.

It is a further object of this invention to provide such a system which directly provides absolute values of crimp recovery and shrinkage.

It is a further object of this invention to provide an improved yarn tension control for precisely maintaining a predetermined tension on a yarn.

This invention results from the realization that a truly effective and simple system can be constructed for determining both recovery potential and fiber shrinkage in a yarn by developing the yarn in a first zone between first and second feeding means, controlling the speed of the second feeding means to maintain a predetermined tension on the yarn in that zone, fully extending the yarn to its predevelopment state in a second zone between the second feeding means and a third feeding means, with the third feeding means having its speed varied to maintain tension by a second yarn tension control, and then comparing the measurable feed rates of the first and second feeding means to establish the total recovery and the second and third feeding means to determine the crimp recovery and comparing the feed rates of the first and third feeding means to determine the fiber shrinkage.

The invention features a yarn tester system including heater means for inducing a change in length of the yarn to be tested. There are first means for feeding yarn to be tested to the heater means at a first predetermined tension and first means for sensing a function of the amount of yarn transferred by the first means for feeding. There is a second means for feeding yarn for receiving yarn from the heater means and second means for sensing a function of the amount of yarn transferred by the second means for feeding. There are third means for feeding yarn for receiving yarn from the second means for feeding, and third means for sensing a function of the amount of yarn transferred by the third means for sensing.

A first yarn tension control means establishes a second predetermined tension on the yarn between the first and second means for feeding and controls the speed of the second means for feeding to maintain the second predetermined tension. Second yarn tension control means establish a third predetermined tension on the yarn between the second and third means for feeding and controls the speed of the third means for feeding to maintain the third predetermined tension. Means responsive to the first, second and third means for sensing determines the fiber shrinkage and yarn recovery of the yarn which is passed through those zones.

In a preferred embodiment the developer is a heater and the yarn is a textured yarn, and the first and third predetermined tensions may be equal. The first means for feeding may include means for setting the first, predetermined yarn tension and it may also include a multi-wrap feeder. The second and the third means for feeding also may each include a multi-wrap feeder. The second means for feeding may include a variable speed pinch roll device. The first yarn tension control means may include support means, a carriage movable relative to the support means, and a tension arm pivotably mounted to the carriage and having means for engaging the yarn. It also includes means for setting the tension arm to apply the second predetermined tension to the yarn, means, responsive to the rotation of the arm indicating a change in yarn flow rate, and means responsive to the means for indicating for moving the carriage relative to the support means to maintain the second predetermined tension. The yarn tension control means may include a yarn delivery system mounted with the carriage at the same level as, and spaced from, the means for engaging the yarn. The yarn delivery system may be positioned between the first means for feeding and the means for engaging the yarn. The yarn delivery system may include a yarn drive device which may be, e.g., a capstan drive or an aspirator drive. The aspirator is oriented with its output directed above the means for engaging the yarn in order to aim the air jet away from the yarn path while directing the yarn to the means for engaging. The second yarn tension control means may be similarly constructed to apply and maintain the third predetermined tension to the yarn. The first and second yarn tension control means may include means responsive to the motion of the carriage for varying the speed of the second and third means for feeding, respectively.

Each of the first, second and third means for feeding may include roll means, and the means for sensing the length of yarn transferred may include a tachometer. The output of the tachometer is proportional to the length of yarn transferred by the feeding means and thus can be used directly to calculate the recovery and shrinkage. In specific constructions the means for sensing may further include converter means responsive to the tachometer for producing linear yarn speed. The converter means may also include means for dividing the linear yarn speed by a period of time to obtain the length of yarn transferred during that period of time.

The means for determining may include means for combining the function of the amount of yarn transferred by the first and second means for feeding to indicate the total recovery of the yarn. The means for determining may further include means for combining the function of the amount of yarn transferred by the second and third means for feeding to indicate the crimp recovery of the yarn. The means for determining may include means for combining the function of the amount of yarn transferred by the first and third means for feeding to indicate the fiber shrink of the yarn.

Also featured in this invention is a yarn tension control means suitable for use with such a testing machine, which includes support means, a carriage movable relative to the support means, and a tension arm pivotably mounted to the carriage and having means for engaging the arm. There are means for setting the tension arm in a neutral position to apply a predetermined tension to the arm. Means responsive to the rotation of the arm indicate an incremental change in yarn tension. Means responsive to the means for indicating move the carriage from an initial position to a compensating position to reestablish the predetermined tension.

The direction of movement of the carriage may be parallel to the tensile force of the yarn on the arm, and there may be means, responsive to the motion of the carriage, for driving a means for varying the speed of a yarn feeding device to produce an offsetting incremental change in yarn feed rate to restore the tension arm to its neutral position. The means for indicating may include a proximity detector.

DISCLOSURE OF PREFERRED EMBODIMENT

Other objects, features and advantages will occur from the following description of a preferred embodiment and the accompanying drawings, in which.

Figure 1:
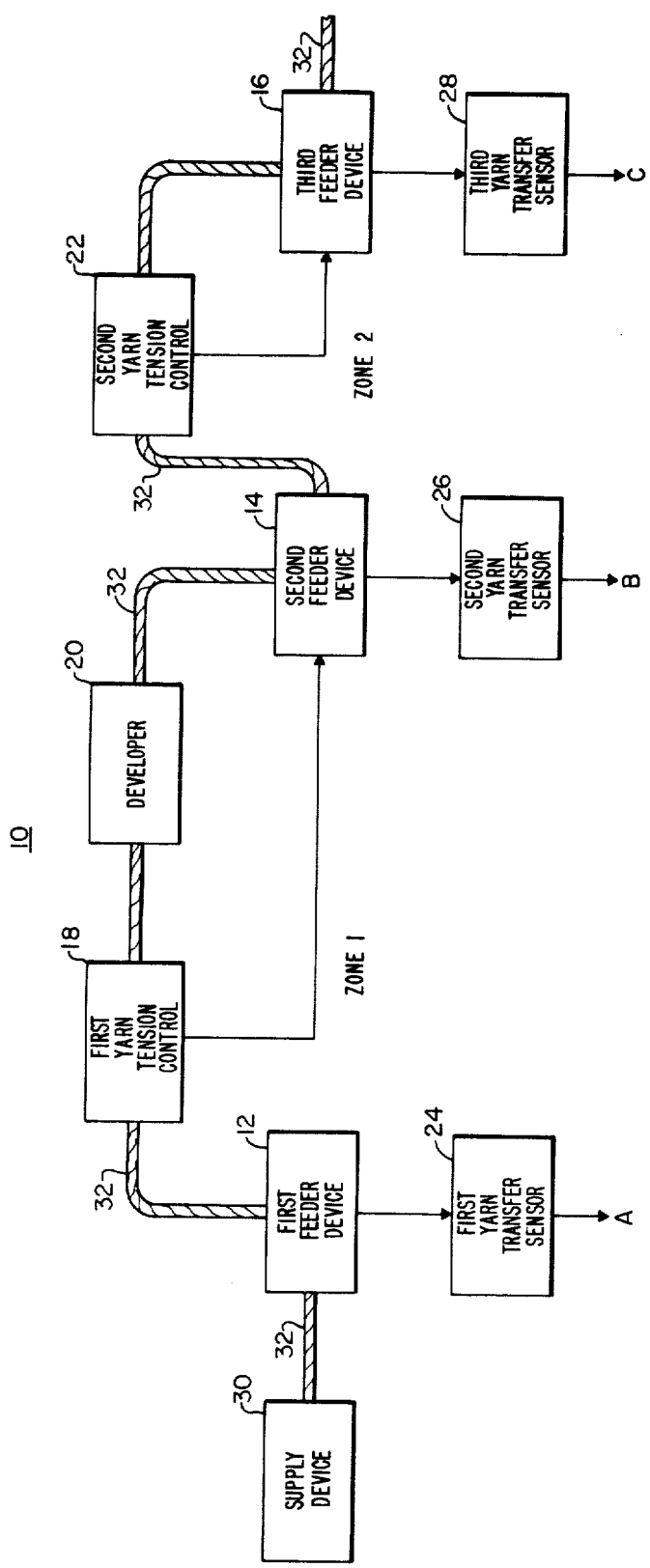
FIG. 1 is a block diagram of a yarn tester system according to this invention.

There is shown in FIG. 1 a yarn tester system 10 according to this invention which includes first and second feeder devices 12 and 14, between which is established tester Zone 1, and a third feeder device 16 which establishes test Zone 2 between it and second feeder device 14. There is also included in Zone 1 a first yarn tension control 18 and developer or heater 20. In Zone 2 there is located a second yarn tension control 22. First, second and third yarn transfer sensors 24, 26, 28 monitor their respective feeder devices 12, 14, and 16 and provide at their outputs A, B, and C a function of the amount of yarn transferred by their corresponding feeder devices. The yarn transfer sensors may measure rotational speed of the feeder devices, linear speed of the yarn, or length of the yarn.

Conventional supply device 30 provides yarn 32 to first feeder device 12 at a predetermined tension set to fully extend the yarn. From first feeder device 12, yarn 32 is delivered to first yarn tension control 18 which maintains a second, much lighter tension on yarn 32 as it is delivered to developer 20, where typically a textured yarn is heated in a completely relaxed or substantially relaxed state to allow it to contract. Also, because of the heat applied in heater 20, some fiber shrinkage occurs. Yarn 32, in this relaxed, contracted state, is then delivered to second feeder device 14 which is run at a slower speed to compensate for the contraction of the yarn in heater 20. If at any time the tension on yarn 32 varies from the second, predetermined tension due to a change in the yarn recovery or shrinkage in heater 20, first yarn tension control 18 immediately acts to reestablish that second predetermined tension by varying the yarn feed rate of second feeder device 14, which also results in an adjustment of the total length of yarn betwen first feeder device 12 and second feeder device 14. The difference in the lengths A and B which have been transferred through first feeder device 12 and second feeder device 14, respectively, are indicative of the total recovery of the yarn in Zone 1.

From second feeder device 14, yarn 32 is fed to second yarn tension control 22 and from there to third feeder device 16. Second yarn tension control 22 maintains a third predetermined tension on the yarn, much higher than the second predetermined tension and often equal to the first predetermined tension. Typically the tension is set to remove the crimp development which occurred in Zone 1. Any momentary variation in that tension due to yarn recovery in Zone 2 is immediately corrected to reestablish that third predetermined tension by varying the yarn feed rate through third feeder device 16, which also results in an adjustment of the loop length of yarn 32 between the second, 14, and third, 16, feeder devices. Yarn 32 is fed to a conventional take-up device after it leaves third feeder device 16. The difference between the amount of yarn, B and C, transferred by second feeder device 14 and third feeder device 16, respectively, is proportional to and indicates the crimp recovery of the yarn in Zone 2. Functions of the amount of yarn include rotary speed, linear speed, or length. Fiber shrinkage is indicated by the difference between the function of the amount of yarn A, passing through first feeder device 12, and C, passing through third feeder device 16.

Figure 2:
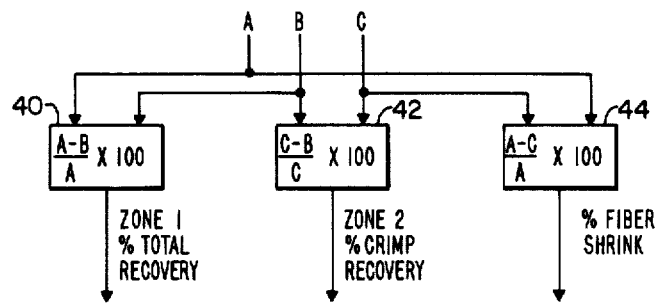
FIG. 2 is a block diagram of a means for calculating recovery and shrinkage with the yarn tester system according to this invention.

The percentage of recovery and shrink may be calculated arithmetically as shown in FIG. 2. Arithmetic circuit 40 subtracts the value B from value A, divides it by A and multiplies it by 100 to obtain the percentage of total recovery of the yarn. Arithmetic circuit 42 subtracts B from C, divides by C, and multiplies by 100 to obtain the percentage of crimp recovery. Arithmetic circuit 44 subtracts C from A, divides by A and multiplies by 100 to obtain the percentage of fiber shrink. These calculations may be done in special circuits, as indicated in FIG. 2, or conveniently they may be done by a microporcessor or small computer.

For example, if a reading is taken when first yarn transfer sensor 24 indicates 10 meters or 1,000 units of yarn have been transferred through first feeder device 12 and it is found that concurrently there were 600 units transferred by feeder device 14 and 900 transferred by feeder device 16, the outputs of transfer sensors 24, 26 and 28 would appear as follows: A=1,000, B=600, C=900. Thus the percent of total recovery would be in Zone 1 (1,000−600)100/1,000, or 40%. The percent of crimp recovery in Zone 2 would be (900−600)100/900, or 33⅓% crimp recovery for a 9 meter or 900 unit length. When adjusted for full 10 meter or 1,000 unit length the crimp recovery is 30%. The fiber shrinkage would be calculated as (1,000−900)/1,000, all multiplied by 100, to yield 10% fiber shrinkage. Thus the crimp recovery, 30%, plus fiber shrinkage, 10%, equals the total recovery of 40%.

With the aid of a computer or microprocessor, further data processing may be performed, for example average or standard deviations, coefficients or variations for multiple samplings, and other analyses may be achieved.

Figure 3:
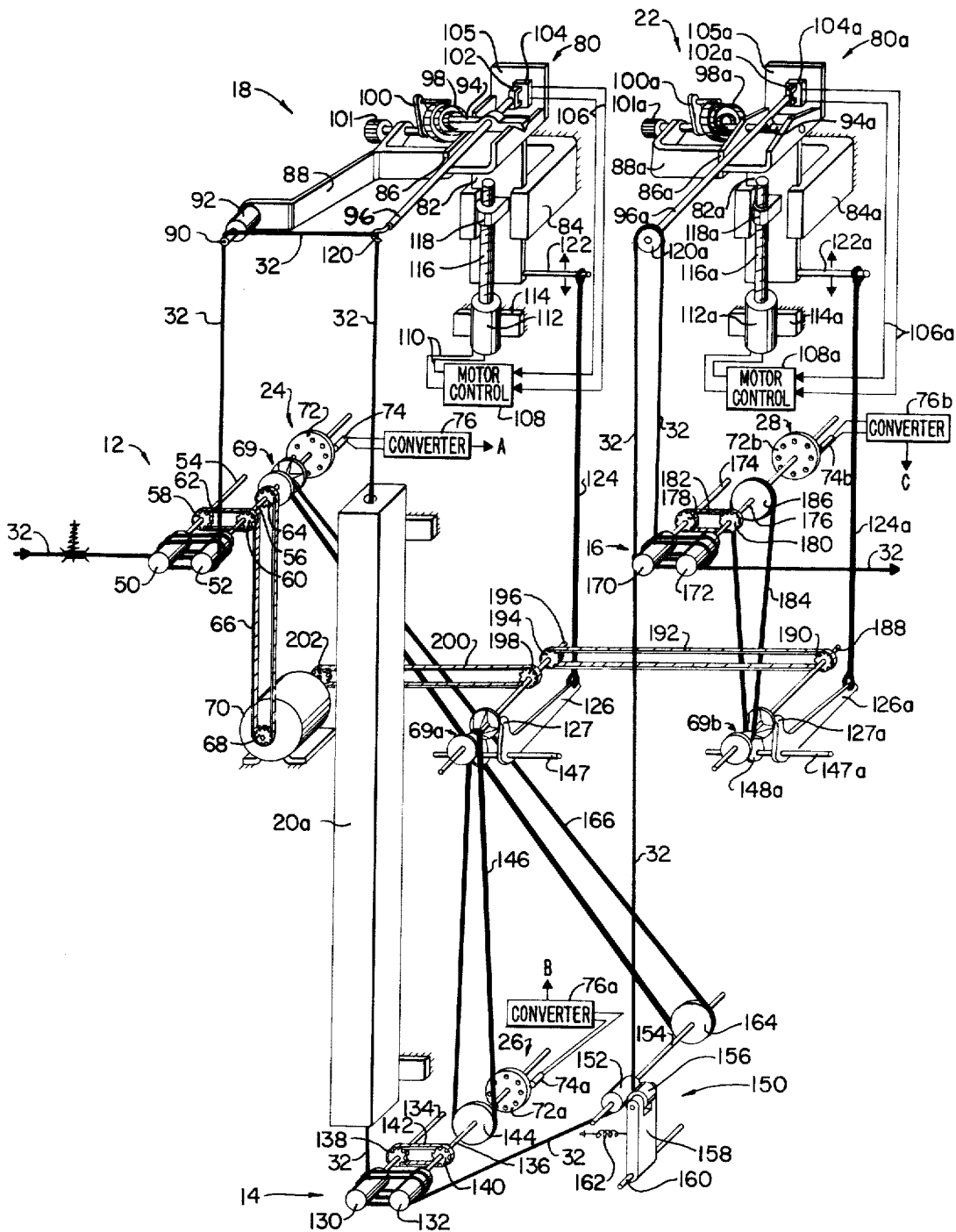
FIG. 3 is a more detailed schematic diagram of the system of FIG. 1.

The system of FIG. 1 is advantageously used to monitor recovery and shrinkage in textured yarn using a heater developer, as indicated in more detail in FIG. 3, where first feeder device 12 includes a tensioning brake such as that disclosed in U.S. Pat. No. 3,575,360, to provide a first predetermined tension, e.g., 10 grams, on yarn 32. First feeder device 12 also includes a multi-wrap feeder, rollers 50, 52, mounted on shafts 54, 56, which contain sprockets 58 and 60 linked by chain 62. Shaft 56 contains sprocket 64 driven by chain 66 interconnected with sprocket 68 on drive motor 70. Also contained on shaft 56 is variable speed pulley system 69 of conventional interlocking wedge design. Also mounted on shaft 56 is first yarn transfer sensor 24, which includes an aperture wheel 72 and photoelectric cell 74, whose output, indicative of the rotational speed of feeder device 12, may be converted to linear speed or length of yarn by converter 76. First yarn tension control 18 includes carriage 80 including a vertical slider member 82 slidably mounted in fixed frame 84, U-shaped channel 86 mounted on top of slider member 82, and support bracket 88 which carries on its outer end capstan 90 and capstan drive motor 92. Capstan 90 has a surface speed rate set in excess of the selected yarn feed speed to frictionally urge the yarn toward the sensing arm 96. The yarn feed speed is selected by adjusting the motor 70 speed. Wedge pivot 94 rests on bearing surfaces on channel 86 and supports tension arm 96. The tension applied to yarn 32 by tension arm 96 is adjustable by means of spiral spring 98 attached to crank control 100 manipulatable by knob 101. The tension is set at 1 to 2 milligrams per denier of yarn under test, e.g., 150 denier-150 milligrams of tension. Magnet 102 mounted to the end of tension arm 96 permits Hall sensor 104, mounted on rear wall 105 of bracket 86, to monitor the rotation of tension arm 96 with pivot wedge 94. Other types of proximity sensors may be used in place of a Hall device and magnet.

Any change in tension on the yarn is detected by the movement of the arm. A change in the position of tension arm 96 is sensed by Hall device 104, whose output on lines 106 is delivered to motor control circuit 108, which through its outputs 110 drives motor 112 mounted to bracket 114. Shaft 116 of stepping motor 112 is driven in a clockwise or counterclockwise rotation, depending upon the direction of rotation of tension arm 96. Rotation of shaft 116, threadably engaged with nut 118, causes slide member 82, as well as the rest of carriage 80, to move relative to frame 84. Carriage 80 is moved up or down in a direction parallel to the tension on yarn 32 as it leaves hook 120 at the end of tension arm 96 as it proceeds through heater 20a. The motion of slider member 82 is conveyed by pin 122 to rod 124 and in turn to crank 126, the function of which, X the operation of first yarn tension control 18, is explained infra.

Second feeder device 14 includes a pair of feed rolls 130, 132, mounted on shafts 134, 136, which carry sprockets 138, 140, linked by chain 142. Also mounted on shaft 136 is pulley 144, driven through belt 146 by variable speed pulley system 69a which, in combination with crank 126 pivotable on shaft 147 mounted on a frame not shown is included in first yarn tension control 18. Also mounted on shaft 136 is second yarn transfer sensor 26 which includes the same parts as yarn transfer sensor device 24.

In operation, as yarn 32 in heater 20a contracts, the hook 120 at the tip of tension arm 96 is pulled downwardly. This moves magnet 102 upwardly so that Hall device 104 sends a signal to motor control 108 to drive motor 112 to move carriage 80 downwardly to reestablish the horizontal orientation of tension arm 96 to maintain the predetermined tension level of 1 to 2 milligrams. This downward movement of carriage 80 accomplishes both goals. The downward motion of carriage 80 allows arm 96 to return to its neutral, horizontal position. At the same time, through pin 122 and rod 124, the end of crank 126 proximate rod 124 moves downwardly so that bearing portion 127 moves clockwise away from the variable speed pulley system 69a and allows the two pulleys to separate same and reduce their effective diameter. This, through belt 146 and pulley 144, reduces the speed of feed rollers 130 and 132, thereby decreasing the yarn take-up rate, resulting in a decrease in the length of yarn between feeder 14 and feeder device 12, and maintaining the tension on yarn 32 at a selected value.

In this manner it is apparent that yarn tension control means 18 acts to adjust the size of the yarn loop which extends from the first feeder device 12 to the second feeder device 14. An increase in shrinkage or recovery in heater 20a momentarily pulls down hook 120. This motion is immediately sensed by Hall device 104 and eliminated by downward movement of carriage 80. The downward movement of carriage 80 through rod 124 decreases the speed of second feeder device 14. This accommodates the increased shrinkage or recovery and shortens the yarn loop between first feeder device 12 and second feeder device 14.

Spring 98 is used in place of a weight to bias arm 96 in order to eliminate inertia and reduce the weight. The servo-loop which resets the arm to the neutral position by repositioning carriage 80 accommodates for the variation in force applied by the spring when it is tensed or relaxed from its original setting. During the adjustment period the tension arm will momentarily be out of its horizontal orientation, which will result in a slight tension error on the yarn during the adjustment period only.

The horizontal path of yarn 32 arriving at hook 120 eliminates any vertical component of tension which would interfere with the precision of the light tension set on yarn 32 leaving hook 120 for heater 20a. To achieve a yarn loop and at the same time a horizontal yarn path to sensing arm 96, a yarn delivery system or guide that moves with carriage 80 is placed to the side of hook 120 to carry the vertical yarn tension components. The yarn delivery system or guide in the instant device includes capstan 90 with its motor 92, which removes the drag of the vertical yarn components to deliver the yarn in its horizontal path essentially tension-free to the hook 120 of tension arm 96. By eliminating all vertical drag on yarn delivered to sensing arm 96—i.e. feeding yarn horizontally—any and all friction of the yarn through hook guide 120 is absorbed in the pivot of sensing arm 96, and the tension in the yarn leaving the sensing arm is fully predictable and is equal to the force moment of the tensioning spring 96. In more conventional, less critical tension control systems such as used on sensing system 22 with its pulley 120a, there are always small unpredictable errors in the tension on one side of the pulley relative to the other due to the bearing drag of the pulley. Further, if pulleys are used, as they must be if tension control is critical, in any conventional system the pulleys themselves add mass to the sensing arm, resulting in a less responsive system. In the horizontal path approach a simple thread guide (hook) may be used, keeping mass to a minimum for maximum responsiveness without unknown guide drags being introduced to the tensioning on the yarn to be controlled.

From feeder rolls 130 and 132, yarn 32 moves through spring-loaded pinch roll or nip roll device 150, which includes roller 152, mounted on shaft 154, and roller 156, attached on member 158, pivotably mounted to shaft 160 and urged toward roller 152 by spring 162. Roller 152 through shaft 154, pulley 164 and belt 166 is driven by variable speed pulley system 69. The nip roll device 150 in second feeder device 14 provides a fixed point in the path of yarn 32 against which yarn 32 may be tensioned to remove the crimp development to Zone 1 in preparation for the Zone 2 measurements. Nip roll device 150 also provides a take-off system for the loosely held yarn on rolls 130, 132 and establishes a constant feed rate to Zone 2 to minimize any sympathetic responses in Zone 2 to the variable output feed rate of rolls 130, 132. Nip roll device 150 is driven at a feed rate slower than that of rolls 50, 52 and faster than that of rolls 130, 132 to remove most but not all of the crimp recovery developed in Zone 1. A rule of thumb for setting the feed rate of nip rolls 150 is to set them to feed at a rate several percent higher than the anticipated shrinkage rate, i.e. slightly slower than the feed rate expected for feeder system 16.

Yarn 32 is delivered next to second yarn tension control 22, which is identical with yarn tension control 18 with the exception that spiral spring 98a is stronger to maintain a higher tension level, usually close to and often equal to the first predetermined tension, e.g 10 grams; tension arm 96a is supported by pivot pin 94a instead of wedge pivot 94; bracket 86a has been configured slightly differently to accommodate pivot pin 94a; a pulley 120a has replaced hook 120, and bracket 88a has been reduced in size since capstan 90 and capstan motor 92 have been eliminated. Third feeder device 16 includes a pair of feed rolls and like parts have been given like numbers accompanied by a lower case a in second yarn tension control 22. Feed rollers 170, 172 in third feeder device 16 are mounted on shafts 174, 176, which contain sprockets 178 and 180 linked by chain 182. Also mounted on shaft 176 is third transfer sensor 28, identical to the other yarn transfer sensors, and pulley 186, whose speed and the speed of feed rollers 170, 172, is controllable by variable-speed pulley system 69b through belt 184 and pulley 186 mounted on shaft 176. Variable-speed pulley system 69b is mounted on shaft 188 driven by sprocket 190 and chain 192. The other end of chain 192 is interconnected with sprocket 194 on shaft 196, which in turn is driven through sprocket 198 and chain 200 by motor 70, which drives chain 200 by means of sprocket 202.

In operation, second yarn tension control 22 operates in the same manner as first yarn tension control 18 to rotate crank 126a and drive the two interlocking wedge pulleys of pulley system 69b in and out, varying the effective pulley diameter and thus the speed with which feed rollers 170, 172 of third feeder device 16 are driven. The various features of yarn tension control 18 may be used in control 22.

In this way, variations in crimp recovery are translated directly to a function of the amount of yarn which is transferred by feeder devices 14 and 16. Thus the outputs of feeder devices 14 and 16 provided as outputs B and C of yarn transfer sensors 26 and 28, may be combined directly with the similar output A from yarn transfer sensor 24 to produce total recovery, crimp recovery and fiber shrink independently and precisely. The feed rolls in the feeder device 14 should, as indicated, be a multiple-wrap design such as a Godet system, and should not be a gripper or a nip-type design which would flatten and push back the fully developed, puffy yarn emerging from the heater which would result in error between the measurable feed rate of the feed rolls and the true speed of the yarn emerging from the heater.

Figure 4:
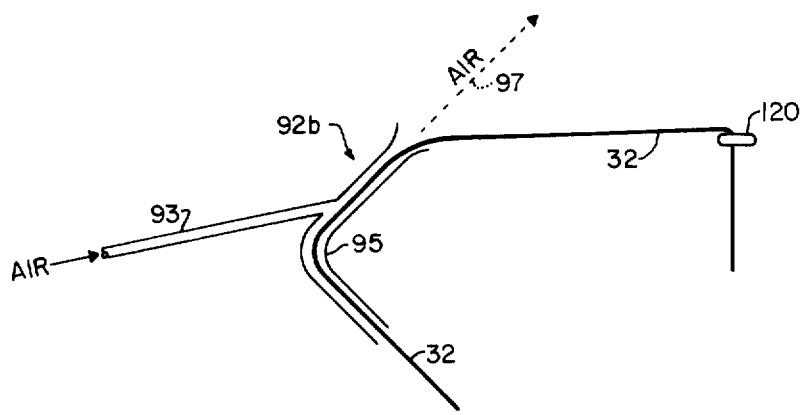
FIG. 4 is a detailed diagram of an alternative delivery system for the yarn in the first yarn tension control.

Capstan drive motor 92 may be replaced by an aspirator or air drive 92b, FIG. 4, driven by a high pressure air source (not shown) through inlet tubing 93 connected to aspirator tube 95. Tube 95 is oriented so that the outflow of pressurized air 97 is directed away from the path of yarn 32 through hook 120 in order to avoid any air flow effects that might introduce unknown moment forces on delicate sensing arm 96, which may be a simple soda straw. The airflow must be adjusted so as not to drive the yarn from the aspirator in an arc, which would upset the horizontal flow of yarn to the sensing arm 96.

Figure 5:
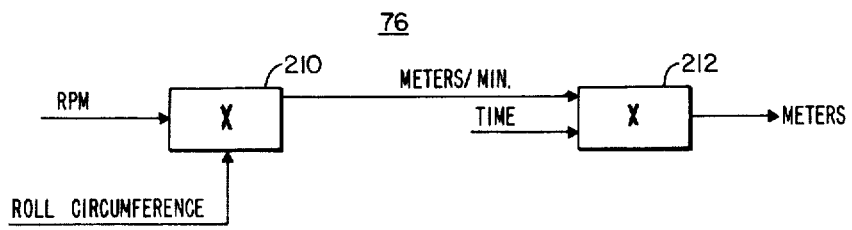
FIG. 5 is a block diagram of a converter shown in FIG. 3.

Converters 76, 76a, 76b each may include a multiplier circuit 210, FIG. 5, which multiplies the tachometer output rpm by roll circumference to obtain a linear speed, for example, in meters per minute. A multiplier circuit 212 multiplies the linear speed by the elapsed time to obtain the length in meters of the yarn fed during that period of time.

Although the preferred embodiment is described with a single motor drive system and multi-wrap feed rolls, this is not a necessary limitation of the invention, as other yarn transport systems, other multi-motor drive systems, and other systems for driving the sensors may be employed. Yarns other than textured yarns that shrink or stretch relative to heat and tension cycling may also be tested in this instrument, and the invention should be understood to cover structures and applications other than those specifically disclosed with respect to this embodiment.

Other embodiments will occur to those skilled in the art and are within the following claims.

What is claimed is:

1. A yarn tester system comprising:
   heater means for inducing a change in length of yarn to be tested;
   first means for feeding yarn to be tested to said heater means at a first predetermined tension;
   first means for sensing a function of the amount of yarn transferred by said first means for feeding;
   second means for feeding yarn for receiving yarn from said heater means;
   second means for sensing a function of the amount of yarn transferred by said second means for feeding;
   third means for feeding yarn for receiving yarn from said second means for feeding;
   third means for sensing a function of the amount of yarn transferred by said third means for sensing;
   first yarn tension control means for establishing a second predetermined tension on said yarn between said first and second means for feeding and controlling the speed of said second means for feeding to maintain said second predetermined tension;
   second yarn tension control means for establishing a third predetermined tension on said yarn between said second and third means for feeding and controlling the speed of said third means for feeding to maintain said third predetermined tension; and
   means, responsive to said first, second, and third means for sensing, for determining fiber shrinkage and recovery of the yarn which has been transferred between the first, second, and third means for feeding.

2. The yarn tester of claim 1 in which said third predetermined tension is equal to said first predetermined tension.

3. The yarn tester of claim 2 in which said yarn is a textured yarn.

4. The yarn tester of claim 1 in which said first means for feeding includes means for setting said first predetermined yarn tension.

5. The yarn tester of claim 1 in which said first means for feeding includes a multi-wrap feeder.

6. The yarn tester of claim 1 in which said second means for feeding includes a multi-wrap feeder.

7. The yarn tester of claim 6 in which said second means for feeding further includes a variable speed pinch roll device.

8. The yarn tester of claim 1 in which said third means for feeding includes a multi-wrap feeder.

9. The yarn tester of claim 1 in which said first yarn tension control means includes support means; a carriage movable relative to said support means; a tension arm pivotably mounted to said carriage and having means for engaging said yarn; means for setting said tension arm to apply said second predetermined tension to said yarn; means, responsive to rotation of said arm, for indicating a change in yarn flow rate; and means, responsive to said means for indicating, for moving said carriage relative to said support means to maintain said second predetermined tension.

10. The yarn tester of claim 9 in which said first yarn tension control means includes means, responsive to motion of said carriage, for varying the speed of said second means for feeding.

11. The yarn tester of claim 9 in which said yarn tension control means includes a yarn delivery system positioned between said first means for feeding and said means for engaging said yarn, mounted with said carriage at the same level as, and spaced from, said means for engaging said yarn.

12. The yarn tester of claim 11 in which said yarn delivery system includes a yarn drive device.

13. The yarn tester of claim 12 in which said yarn drive device includes a capstan drive.

14. The yarn tester of claim 12 in which said yarn drive device includes an aspirator drive.

15. The yarn tester of claim 14 in which said aspirator drive is oriented with its output directed above said means for engaging said yarn in order to aim the air jet away from the yarn path while directing the yarn to said means for engaging.

16. The yarn tester of claim 1 in which said second yarn tension control means includes support means; a carriage movable relative to said support means; a tension arm pivotably mounted to said carriage and having means for engaging said yarn; means for setting said tension arm to apply said third predetermined tension to said yarn; means, responsive to rotation of said arm, for indicating a change in yarn flow rate; and means, responsive to said means for indicating, for moving said carriage relative to said support means to maintain said third predetermined tension.

17. The yarn tester of claim 16 in which said second yarn tension control means includes means, responsive to motion of said carriage, for varying the speed of said third means for feeding.

18. The yarn tester of claim 1 in which each said first, second and third means for feeding includes roll means and said means for sensing the length of yarn transferred includes a tachometer.

19. The yarn tester of claim 18 in which said means for sensing further includes converter means responsive to said tachometer to produce a linear yarn speed.

20. The yarn tester of claim 19 in which said converter means includes means for dividing the linear yarn speed by a period of time to obtain the length of yarn transferred during that period of time.

21. The yarn tester of claim 1 in which said means for determining includes means for combining the function of the amount of yarn transferred by said first and second means for feeding to indicate the total recovery of the yarn.

22. The yarn tester of claim 1 in which said means for determining includes means for combining the function of the amount of yarn transferred by said second and third means for feeding to indicate the crimp recovery of the yarn.

23. The yarn tester of claim 1 in which said means for determining includes means for combining the function of the amount of yarn transferred by said first and third means for feeding to indicate the fiber shrink of the yarn.

24. A yarn tension control means for a yarn testing machine having means for varying the speed of a yarn feeding device, comprising:
support means;
a carriage movable relative to said support means;
a tension are pivotably mounted to said carriage and having means for engaging the yarn;
means for setting the tension arm in a neutral position to apply a predetermined tension to the yarn;
means, responsive to rotation of said arm, for indicating an incremental change in yarn tension;
means, responsive to said means for indicating, for moving said carriage from an initial position to a compensating position to re-establish said predetermined tension; and
means, responsive to the motion of said carriage, for driving said means for varying the speed of a yarn feeding device to produce an offsetting incremental change in yarn feed rate to restore said tension arm to its neutral position.

25. The yarn tension control means of claim 24 further including a yarn delivery system mounted with said carriage at the same level as, and spaced from, said means for engaging the yarn.

26. The yarn tester of claim 25 in which said yarn delivery system includes a yarn drive device.

27. The yarn tester of claim 26 in which said yarn drive device includes a capstan drive.

28. The yarn tester of claim 26 in which said yarn drive device includes an aspirator drive.

29. The yarn tester of claim 28 in which said aspirator drive is oriented with its output directed above said means for engaging said yarn in order to aim the air jet away from the yarn path while directing the yarn to said means for engaging.

30. A yarn tension control means comprising:
support means;
a carriage movable relative to said support means;
a tension arm pivotably mounted to said carriage and having means for engaging the yarn;
means for setting the tension arm in a neutral position to apply a predetermined tension to the yarn;
means, responsive to rotation of said arm, for indicating an incremental change in yarn tension; and
means, responsive to said means for indicating, for moving said carriage from an initial position to a compensating position to re-establish said predetermined tension.

31. The yarn tension control means of claim 30 in which the direction of movement of said carriage is parallel to the tensile force on the yarn on said arm.

32. The yarn tension control means of claim 30 in which said means for indicating includes a proximity detector.

* * * * *